United States Patent [19]
Bernard

[11] Patent Number: 5,989,615
[45] Date of Patent: Nov. 23, 1999

[54] ENZYME INFUSION PROCESS FOR PREPARING WHOLE PEELED CITRUS FRUIT

[76] Inventor: Andre Bernard, Five Kitchel Rd., Mt. Kisco, N.Y. 10549

[21] Appl. No.: 09/105,357

[22] Filed: Jun. 26, 1998

[51] Int. Cl.⁶ ........................................ A23L 1/10
[52] U.S. Cl. .............................. 426/482; 426/50; 426/52; 426/287; 426/616
[58] Field of Search ................ 426/50, 52, 287, 426/482, 616

[56] References Cited

U.S. PATENT DOCUMENTS 4,284,651  8/1981  Bruemmer ................ 426/50
5,200,217  4/1993  Elliott et al. .................... 426/50

Primary Examiner—Anthony J. Weier
Attorney, Agent, or Firm—Myron Amer P.C.

[57] ABSTRACT

The removal of albedo in the preparation of a citrus fruit for consumption, in which a known aqueous solution of pectinase enzyme is used for its known albedo-removal function, but in the present circumstances a vacuum is used to primarily draw the pectinase enzyme to the interface of the albedo and the citrus fruit and only nominally to the interface of the albedo and the peel of the citrus fruit, so that removal of the peel carries with it the albedo and uncovers the citrus fruit in a desirable albedo-free condition.

1 Claim, 1 Drawing Sheet

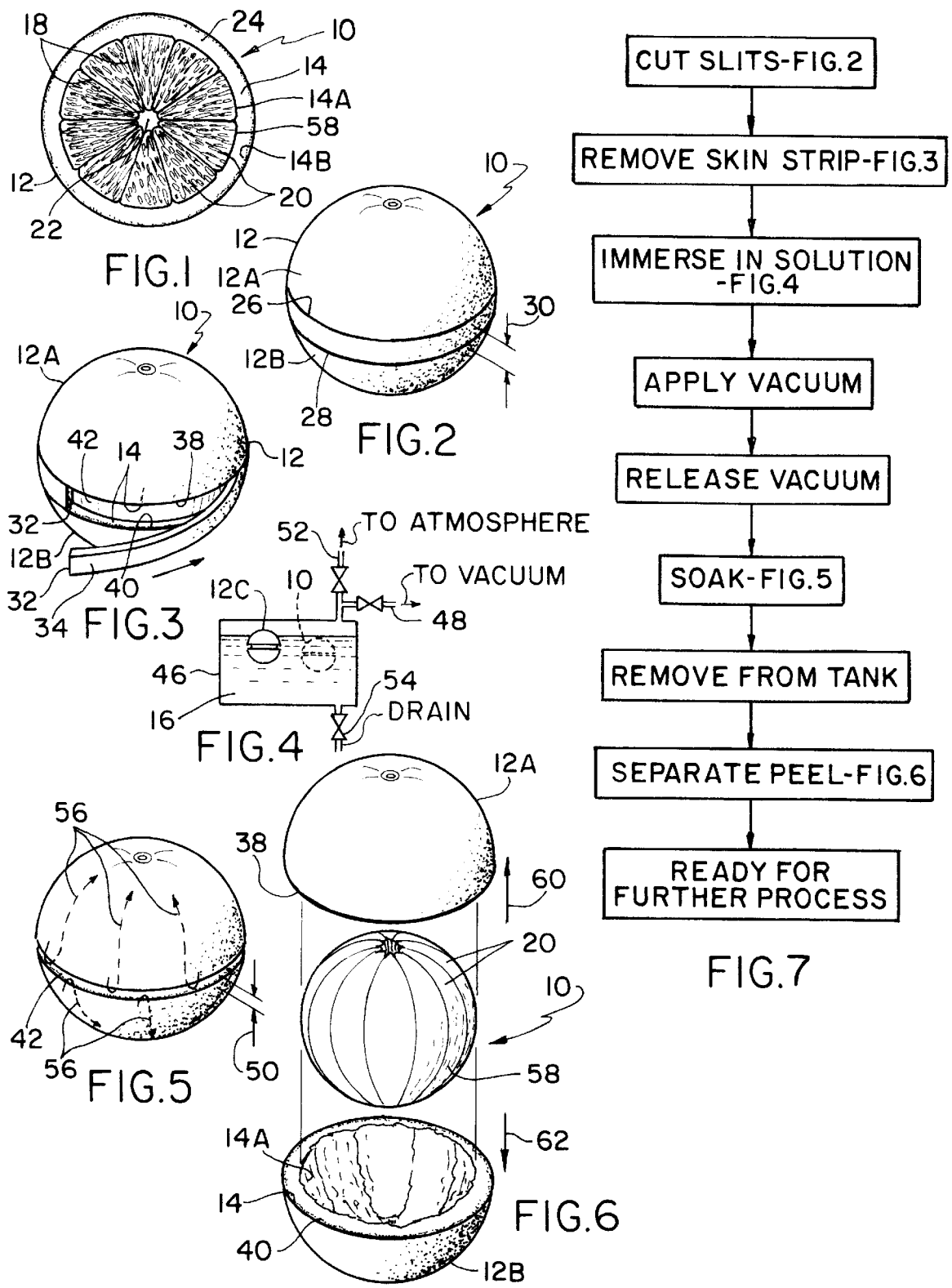

ENZYME INFUSION PROCESS FOR PREPARING WHOLE PEELED CITRUS FRUIT

The present invention relates generally to removal of albedo, a known growth component of citrus fruit, and, more particularly, relates to a citrus fruit-processing method that results, for all intents and purposes, in an albedo-free citrus fruit in condition for point-of-sale and/or consumption.

EXAMPLE OF THE PRIOR ART

It is known, by common experience, that a citrus fruit has an external peel protecting the citrus fruit contained therein, and a growth of a layer of albedo in an interposed position between the peel and fruit having an outboard surface in attached relation to the peel and an inboard surface in attached relation to the fruit.

The patented literature instructs the use of an aqueous solution of a pectinase enzyme which ingests and consequently removes the albedo during the processing of the citrus fruit, one such prior patent being U.S. Pat. No. 5,200,217 issued to Elliott et al. for "Enzyme Infusion Process for Preparing Whole Peeled Citrus Fruit" on Apr. 6, 1993. However, the '217 patent and all other known patents leave it to chance whether the enzyme will weaken the attachment of its outboard surface to the peel, or will weaken the attachment of its inboard surface to the fruit. Only if the attachment is weakened at the interface of the albedo inboard surface and the fruit will the removal of the peel carry with it the albedo and thus result in an uncovered fruit that is substantially albedo-free.

Broadly, it is an object of the present invention to provide a citrus fruit processing method overcoming the foregoing and other shortcomings of the prior art.

More particularly, it is an object to prepare the citrus fruit, using vacuum and related technology, so that detachment occurs at the albedo surface that results in albedo-free fruit, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a plan view of a citrus fruit processed in accordance with the within inventive method, shown in half section to better illustrate the internal growth components thereof;

FIG. 2 is an isometric view of the citrus fruit illustrating the first step of said method;

FIG. 3 is a view similar to FIG. 2, but illustrating the method third step;

FIG. 4 is a schematic diagram of apparatus useful for practicing the within method;

FIG. 5 is a view similar to FIG. 2, but illustrating a subsequent method step;

FIG. 6 is an exploded isometric view of a processed citrus fruit; and

FIG. 7 is a flow chart correlating the method steps to the drawing figures and labeled to identify the method steps.

In the processing of citrus fruit, such as an orange or grapefruit or the like, in condition for sale or consumption, it is desirable to remove from the fruit 10 its external peel 12 and, most importantly, a growth component of albedo 14 having an interposed position between the peel 12 and fruit 10. It is already well known that albedo 14 is ingested and consequently removed by a pectinase enzyme solution 16 and is employed to this end in citrus fruit processing, all as is fully described and illustrated in U.S. Pat. No. 5,200,217 issued to Elliot et al. for "Enzyme Infusion Process for Preparing Whole Peeled Citrus Fruit" on Apr. 6, 1993, which '217 patent by this reference is incorporated herein in its entirety.

Underlying the present invention is the recognition that two flow paths for the enzyme solution can be established in a fruit-processing method, one more resistant to flow than the other, and the causing of the enzyme solution to follow the path of least resistance which is between the albedo 14 and the fruit 10, with the result that the fruit 10 after being uncovered of its peel 12 has a desirable nominal growth of albedo 14 in covering relation over the fruit 10.

As best understood from FIG. 1, a citrus fruit 10 has, as already noted, external peel 12, an intermediate growth of albedo 14 and, in its center, the fruit "meat" itself, the latter consisting of a membrane 18 of wax encasing juice sacs 20, air spaces 22, and air pockets 24.

In the first method step, as illustrated in FIG. 2, two slits 26 and 28 spaced apart the distance 30, preferable about ⅜ inch for a "navel" orange, are cut to half the depth of the albedo 14. Next, as illustrated in FIG. 3, the slits 26 and 28 are transversely cut, as at 32, enabling the removal of peel 12 as a strip 34 which exposes the albedo 14, as at 36, and produces edges 38 and 40 which bound a slot 42 caused by the removal of the strip 34 and which edges function as gripping surfaces in the removal of the peel halves 12A and 12B, producing, as best shown in FIG. 6, an albedo-free fruit 10.

In the processing of the fruit 10 to the FIG. 6 condition, desirable for sale and/or consumption, use is made of a tank 46 for the enzyme solution 16 into which the citrus fruit in an initial condition, as noted by 12C, is immersed, then subjected to a selected vacuum through vacuum connection 48, which modifies the immersed citrus fruit to the narrowed-width condition to about ⅛ inch, as noted by 50, as a consequence of removal of air from the air space 22, air pockets 24, and otherwise a part of the citrus fruit growth components. The applied vacuum 48 is released to atmosphere, as noted at 52, which causes an initial inflow of the enzyme solution 16 into the slot 42 and into ingesting relation to the exposed albedo 14. The time of soaking of the citrus fruit 10 is recommended for 3–4 minutes, afterwhich the solution is drained, as at 54, facilitating the removal of the citrus fruit 10.

In practice, it has been found, as illustrated in FIG. 5, that the path of least resistance noted by the reference arrows 56, is between the albedo inner surface 14A in attached contact with the relatively slippery membrane surface 58 rather than the more resistant-to-flow albedo outer surface 14B in attached contact with the peel 12. The peel 12 is then removed in two halves 12A and 12B by opposite direction forces 60 and 62, and since encountered albedo 14 is ingested by the pectinase enzyme dissolved in the solution 16 along the path of least resistance 56, the uncovered citrus fruit 10 is in the illustrated albedo-free condition of FIG. 6.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

what is claimed is:

1. A method of processing a peeled citrus fruit having an external peel, an internal fruit encased in a fluid-impervious membrane cover, and an albedo growth in an interposed position between said peel and said membrane-covered fruit, said albedo growth having an outer surface in attached relation to said peel and an inner surface in attached relation to said membrane-covered fruit, said processing method comprising the steps of recognizing a first flow path at an interface of said outer surface of said albedo growth and said peel having a resistance to flow therethrough, recognizing a second flow path at an interface of said albedo growth and said membrane-covered fruit having a lesser resistance to flow therethrough attributable to a slippery nature of said fruit membrane cover, removing a hemispherical slot through said peel and said albedo growth so as to expose said first and second flow paths and to present gripping surfaces in edges of said peel bounding said hemispherical slot, immersing said citrus fruit in a pectinase enzyme solution, applying a vacuum to said citrus fruit-immersed solution so as to withdraw air from said citrus fruit, releasing said vacuum so as to cause said enzyme solution to initially flow into said hemispherical slot preparatory to subsequent flow in processing relation to said albedo growth, flowing primarily along said second flow path as a path of least resistance said initial-inflowing enzyme solution, such that said pectinase enzyme causes detachment of said membrane cover from said inner surface of said albedo growth and leaves intact said outer surface thereof attached to said peel, and applying opposite direction forces to said gripping surfaces causing removal of said peel with albedo growth attached thereto and thereby providing an uncovered fruit with minimal albedo growth.

* * * * *